United States Patent
Gerber et al.

(10) Patent No.: US 8,788,055 B2
(45) Date of Patent: Jul. 22, 2014

(54) MULTI-LOCATION POSTURE SENSING

(75) Inventors: Martin T. Gerber, Maple Grove, MN (US); John C. Rondoni, Plymouth, MN (US)

(73) Assignee: Medtronic, Inc., Minneapolis, MN (US)

( * ) Notice: Subject to any disclaimer, the term of this patent is extended or adjusted under 35 U.S.C. 154(b) by 1016 days.

(21) Appl. No.: 11/800,653

(22) Filed: May 7, 2007

(65) Prior Publication Data

US 2008/0281381 A1    Nov. 13, 2008

(51) Int. Cl.
*A61N 1/36* (2006.01)
*A61N 1/05* (2006.01)

(52) U.S. Cl.
CPC .......... *A61N 1/36135* (2013.01); *A61N 1/0551* (2013.01)
USPC .......................................................... 607/62

(58) Field of Classification Search
USPC .......................................................... 607/62
See application file for complete search history.

(56) References Cited

U.S. PATENT DOCUMENTS

| | | | |
|---|---|---|---|
| 5,233,984 A | 8/1993 | Thompson | |
| 5,342,409 A | 8/1994 | Mullett | |
| 5,593,431 A | 1/1997 | Sheldon | |
| 5,851,193 A | 12/1998 | Arikka et al. | |
| 6,044,297 A | 3/2000 | Sheldon et al. | |
| 6,449,508 B1 | 9/2002 | Sheldon et al. | |
| 6,659,968 B1 | 12/2003 | McClure | |
| 6,834,436 B2 * | 12/2004 | Townsend et al. | 33/512 |
| 7,151,961 B1 | 12/2006 | Whitehurst et al. | |
| 7,155,279 B2 | 12/2006 | Whitehurst et al. | |
| 7,167,743 B2 | 1/2007 | Heruth et al. | |
| 7,167,751 B1 | 1/2007 | Whitehurst et al. | |
| 7,313,440 B2 * | 12/2007 | Miesel | 607/19 |
| 7,542,803 B2 * | 6/2009 | Heruth et al. | 607/46 |
| 2002/0169485 A1 | 11/2002 | Pless et al. | |
| 2002/0170193 A1 | 11/2002 | Townsend et al. | |
| 2003/0149457 A1 | 8/2003 | Tcheng et al. | |
| 2004/0015103 A1 | 1/2004 | Aminian et al. | |
| 2004/0225332 A1 * | 11/2004 | Gebhardt et al. | 607/17 |

(Continued)

FOREIGN PATENT DOCUMENTS

| | | |
|---|---|---|
| EP | 1 195 139 A1 | 4/2002 |
| WO | 03/065891 A2 | 8/2003 |

OTHER PUBLICATIONS

U.S. Appl. No. 11/414,625, filed Apr. 28, 2006, entitled, "Closed-Loop Therapy Adjustment," by Bourget et al.

(Continued)

*Primary Examiner* — Christopher D Koharski
*Assistant Examiner* — Jeremiah Kimball
(74) *Attorney, Agent, or Firm* — Shumaker & Sieffert, P.A.

(57) ABSTRACT

Techniques for controlling therapy delivery based on the relative orientation and/or motion of a device accelerometer and a lead accelerometer are described. In one embodiment, a therapy system includes an electrical stimulator and a lead. The electrical stimulator comprises a processor that controls delivery of a therapy to a target stimulation site in a patient and a device accelerometer coupled to the electrical stimulator. The lead is coupled to the electrical stimulator to deliver the therapy from the electrical stimulator to the target stimulation site in the patient, and includes a lead accelerometer. The processor compares signals from the accelerometers, and controls delivery of the therapy to the patient based on the comparison. In this manner, the processor may adjust stimulation to, for example, address movement of electrodes relative to target tissue when a patient changes postures.

27 Claims, 7 Drawing Sheets

(56) References Cited

U.S. PATENT DOCUMENTS

| | | |
|---|---|---|
| 2005/0060001 A1* | 3/2005 | Singhal et al. .................. 607/19 |
| 2005/0126026 A1 | 6/2005 | Townsend et al. |
| 2005/0209645 A1 | 9/2005 | Heruth et al. |
| 2005/0234514 A1 | 10/2005 | Heruth et al. |
| 2006/0235289 A1 | 10/2006 | Wesselink et al. |
| 2006/0247739 A1 | 11/2006 | Wahlstrand et al. |
| 2006/0259099 A1 | 11/2006 | Goetz et al. |
| 2007/0038265 A1 | 2/2007 | Tcheng et al. |
| 2007/0073355 A1 | 3/2007 | Dilorenzo |

OTHER PUBLICATIONS

U.S. Appl. No. 11/607,454, filed Dec. 1, 2006, entitled, "Closed-Loop Therapy Adjustment," by Bourget et al.

U.S. Appl. No. 11/607,426, filed Dec. 1, 2006, entitled, "Closed-Loop Therapy Adjustment," by Bourget et al.

U.S. Appl. No. 11/799,035, filed Apr. 30, 2007, entitled, "Therapy Adjustment," by Gerber et al.

U.S. Appl. No. 11/799,112, filed Apr. 30, 2007, entitled, "Therapy Adjustment," by Gerber et al.

Notification of Transmittal of the International Search Report and the Written Opinion of the International Searching Authority, or the Declaration dated Aug. 11, 2008 for corresponding PCT Application No. PCT/US2008/061100 (15 pgs.).

Reply to Written Opinion dated Mar. 5, 2009 for corresponding PCT Application No. PCT/US2008/061100 (11 pgs.).

Notification of Transmittal of the International Preliminary Report on Patentability dated Apr. 8, 2009 for corresponding PCT Application No. PCT/US2008/061100 (12 pgs.).

* cited by examiner

FIG. 6

MULTI-LOCATION POSTURE SENSING

TECHNICAL FIELD

The invention relates to electrical stimulation therapy and, more particularly, to controlling electrical stimulation therapy.

BACKGROUND

Electrical stimulators may be used to deliver electrical stimulation therapy to patients to treat a variety of symptoms or conditions such as chronic pain, tremor, Parkinson's disease, epilepsy, urinary or fecal incontinence, sexual dysfunction, obesity, or gastroparesis. An electrical stimulator may deliver stimulation therapy via leads that include electrodes located, as examples, proximate to the spinal cord, pelvic nerves, or stomach, on or within the brain, or within the pelvic floor. In general, the electrical stimulator delivers stimulation therapy in the form of electrical pulses or substantially continuous-time signals. The electrical stimulator may be external or implanted, for example, in a chest cavity, lower back, lower abdomen, or buttocks of a patient.

A clinician selects values for a number of programmable therapy parameters in order to define the stimulation therapy to be delivered to a patient. For example, the clinician may select an amplitude, which may be a current or voltage amplitude. When therapy is delivered in the form of electrical pulses, the clinician may also select a pulse width for a stimulation waveform to be delivered to the patient as well as a rate at which the pulses are to be delivered to the patient. The clinician may also select particular electrodes within an electrode set to be used to deliver the pulses or continuous-time signal, and the polarities of the selected electrodes. The selected electrodes and their polarities may be referred to as an electrode combination or configuration. A group of parameter values may be referred to as a program in the sense that they drive the electrical stimulation therapy to be delivered to the patient.

SUMMARY

In general, the invention is directed to techniques for detecting posture of a patient, and providing or adjusting therapy based on detected postures. More particularly, the invention is directed to techniques that may include detecting relative orientation of and/or motion between a device accelerometer and a lead accelerometer, and controlling stimulation therapy based on the relative orientation and/or motion. The device accelerometer may be located within or coupled to the housing of an electrical stimulator coupled to the lead, and the lead accelerometer may be located within or coupled to the lead. In some embodiments, the lead accelerometer is positioned proximate to a distal end of the lead.

When a patient changes posture, a lead connected to the electrical stimulator may move relative to a target stimulation site. More particularly, the electrodes on the lead that deliver therapy to the target stimulation site may move relative to the target stimulation site, which may change how the patient perceives the therapy. The relative orientation of and/or motion between a device accelerometer and a lead accelerometer may be used to detect this movement and modify the therapy delivered to the patient appropriately.

In one embodiment, the invention is directed to a system comprising an electrical stimulator comprising a device accelerometer, a lead coupled to the electrical stimulator to deliver stimulation from the electrical stimulator to a target stimulation site in a patient, the lead comprising a lead accelerometer, a processor that receives a first signal from the device accelerometer and a second signal from the lead accelerometer, compares the first and second signals, and controls delivery of the stimulation to the patient based on the comparison, wherein the comparison of the first and second signals is indicative of a posture or posture transition of the patient.

In another embodiment, the invention is directed to a method comprising receiving a first signal from a device accelerometer and a second signal from a lead accelerometer, wherein the device accelerometer is located on or within an electrical stimulator that delivers stimulation to a patient, and wherein the lead accelerometer is coupled to a lead that delivers the stimulation from the electrical stimulator to the target stimulation site of the patient. The method further comprises comparing the first and second signals, and controlling delivery of the stimulation by the electrical stimulator based on the comparison, wherein the comparison is indicative of a posture or posture transition of the patient.

In another embodiment, the invention is directed to a medical device comprising a therapy module to deliver stimulation to a patient via a lead, a device accelerometer, and a processor to receive a first signal from the device accelerometer and a second signal from a lead accelerometer on the lead, compare the first and second signals, and control delivery of the stimulation by the therapy module based on the comparison.

The details of one or more embodiments of the invention are set forth in the accompanying drawings and the description below. Other features, objects, and advantages of the invention will be apparent from the description and drawings, and from the claims.

DETAILED DESCRIPTION

Figure 1:
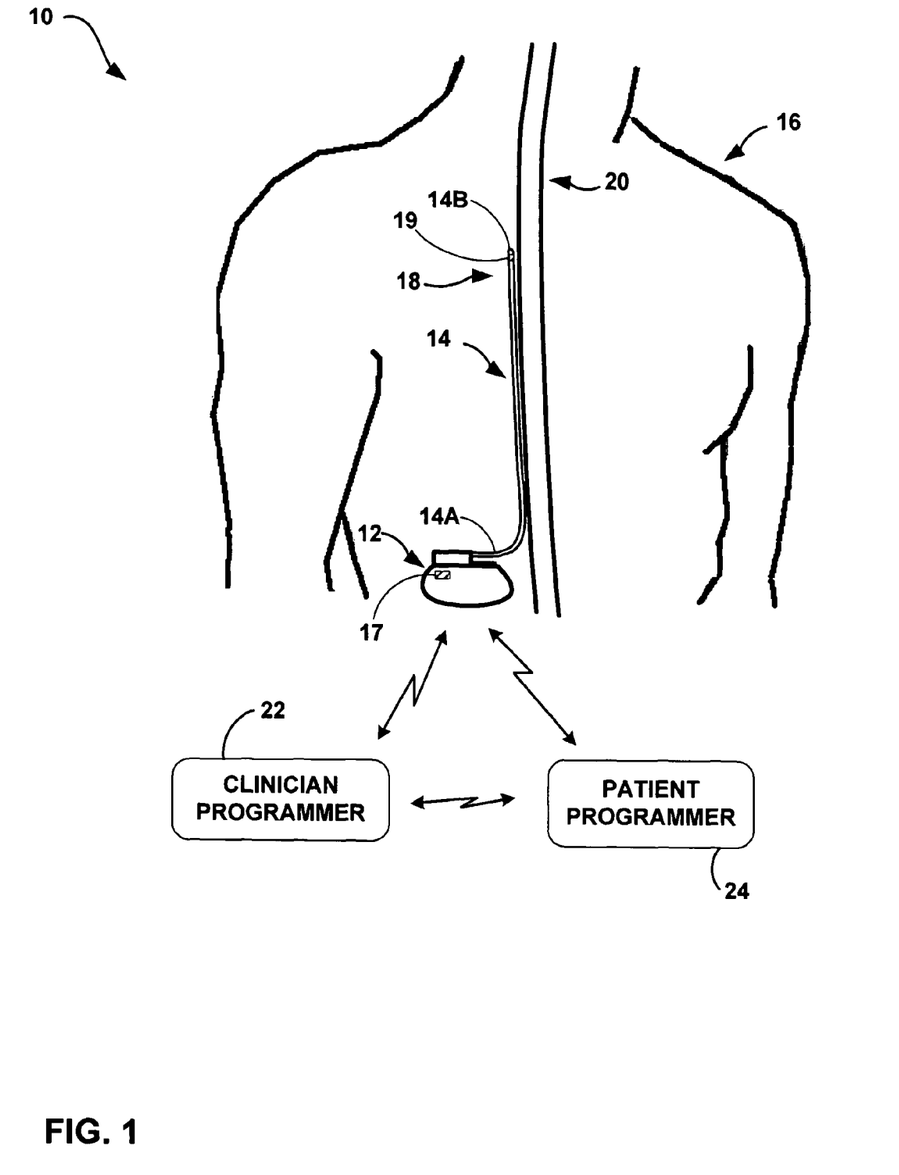
FIG. 1 is a conceptual diagram of a therapy system, which includes an implanted electrical stimulator coupled to a medical lead that has been implanted proximate to a target stimulation site.

FIG. 1 is a conceptual diagram illustrating a therapy system 10, which includes electrical stimulator 12 coupled to stimulation lead 14. Electrical stimulator 12 provides a programmable stimulation signal (e.g., in the form of electrical pulses or substantially continuous-time signals) that is delivered to target stimulation site 18 by lead 14, and more particularly, via one or more stimulation electrodes carried by lead 14. Electrical stimulator 12 may also be referred to as a signal generator. Stimulator 12 may be implantable. For example, stimulator 12 may be subcutaneously implanted in the body of a patient 16 (e.g., in a chest cavity, lower back, lower abdomen, or buttocks of patient 16).

In the example of FIG. 1, electrical stimulator 12 is a neurostimulator that delivers stimulation to nervous tissue at target stimulation site 18. More particularly, stimulator 12 delivers spinal cord stimulation) to target stimulation site 18 of the spinal cord 20 of patient 16. Spinal cord stimulation may be used, for example, to reduce pain experienced by patient 16.

Therapy system 10, however, may be useful in other neurostimulation applications, including pelvic floor stimulation, deep brain stimulation, cortical surface stimulation, neuronal ganglion stimulation, gastric stimulation, peripheral nerve stimulation, or subcutaneous stimulation. Such therapy applications may be targeted to a variety of disorders such as chronic pain, peripheral vascular disease, angina, headache, tremor, depression, Parkinson's disease, epilepsy, urinary or fecal incontinence, sexual dysfunction, obesity, or gastroparesis. Further, therapy system 10 may be useful in non-neuostimulation contexts. For example, stimulator 12 may be used to deliver stimulation to a target muscle tissue site via leads to, for example, provide functional electrical stimulation. Therapy system 10 may be useful in any stimulation application in which movement of lead-borne electrodes relative to a stimulation site and relative motion between a lead coupled to an electrical stimulator and the electrical stimulator may occur. Thus, in various embodiments, target stimulation site 18 may be any nerve or other tissue site in body 16.

In the embodiment illustrated by FIG. 1, stimulator 12 is coupled to a single lead 14. In some embodiments, stimulator 12 may be coupled to two or more leads, e.g., for bilateral or multi-lateral stimulation. Lead 14 includes a lead body that extends from proximal end 15A to distal end 15B. Proximal end 15A of lead 14 may be both electrically and mechanically coupled to stimulator 12 either directly or indirectly (e.g., via a lead extension). In particular, conductors disposed in the lead body may electrically connect stimulation electrodes adjacent to distal end 15B of lead 14 to stimulator 12. Lead 14 may also include one or more lead anchors, e.g., tines, adhesives, sutures, or any other suitable anchors (not shown in FIG. 1), along its lead body to help prevent migration of lead 14.

Stimulator 12 includes device accelerometer 17, and lead 14 includes lead accelerometer 19 (shown with exaggerated size for clarity). In a preferred embodiment, device accelerometer 17 and lead accelerometer 19 are multi-axis accelerometers. However, in some embodiments, device accelerometer 17 and lead accelerometer 19 may be single-axis accelerometers capable of detecting motion along one axis.

Device accelerometer 17 may be located within or coupled to the housing of stimulator 12 such that device accelerometer 17 detects motion of stimulator 12. Lead accelerometer may be located within or coupled to lead 14 such that lead accelerometer 19 detects motion of lead 14. In the illustrated embodiment, lead accelerometer 19 is positioned proximate to distal end 15B of lead 14. The relative motion between device accelerometer 17 and lead accelerometer 19 may reflect the motion of electrodes proximate to distal end 15B of lead 14 relative to target stimulation site 18 when patient 16 changes posture.

A single accelerometer may provide basic motion and body posture information, e.g., standing, walking, prone. However, using a single accelerometer, it is difficult to distinguish between whole body motion (e.g., a bumpy car ride) and actual body movements (e.g., running). Additionally, an accelerometer at a single location, whether or not a multi-axis accelerometer, may be unable to detect certain types of motion or postures of a patient that affect the location of electrodes relative to target tissue. For example, a signal from an accelerometer within a stimulator implanted in the lower back or buttocks region of a patient may not reflect bending or other torsional movements of the torso of the patient, as such motion generally occurs above the lower back. Such movements may cause electrodes at a different location on a lead coupled to the stimulator to move significantly relative to a target stimulation site. For example, electrodes on a lead implanted in the epidural space may move significantly relative to target tissue of the spinal cord when the patient moves in this manner.

In the illustrated embodiment, the relative position of, orientation of, and/or motion between device accelerometer 17 and lead accelerometer 19 may be used as an indication of such movements, and the postures of patient 16 resulting from such movements. Stimulator 12, or another component of system 10, may adjust the therapy delivered to patient 16 based on the relative position of, orientation of, and/or motion between accelerometers 17, 19, as reflected in the signals generated by the accelerometers. The signals generated by of each of accelerometers 17, 19 may change differently as relative motion occurs between the accelerometers due to posture changes by patient.

The electrodes selected to deliver therapy to patient 16, for example, may be adjusted based on the relative motion between accelerometers 17, 19. Additionally or alternatively, one or more other therapy parameters may be adjusted based on the relative motion. In this manner, system 10 may compensate for the movement of electrodes carried by lead 14 relative to target site 18 when patient 16 changes posture.

Therapy system 10 may also include a clinician programmer 22 and a patient programmer 24. Clinician programmer 22 may be a handheld computing device that permits a clinician to program neurostimulation therapy for patient 16, e.g., using input keys and a display. For example, using clinician programmer 22, the clinician may specify therapy parameters, e.g., programs, for use in delivery of neurostimulation therapy. Clinician programmer 22 supports telemetry (e.g., radio frequency telemetry) with neurostimulator 12 to download neurostimulation parameters and, optionally, upload operational or physiological data stored by stimulator 12. In this manner, the clinician may periodically interrogate stimulator 12 to evaluate efficacy and, if necessary, modify the stimulation parameters.

Like clinician programmer 22, patient programmer 24 may be a handheld computing device. Patient programmer 24 may also include a display and input keys to allow patient 16 to interact with patient programmer 24 and stimulator 12. In this manner, patient programmer 24 provides patient 16 with an interface for control of neurostimulation therapy delivered by stimulator 12. For example, patient 16 may use patient programmer 24 to start, stop or adjust neurostimulation therapy. In particular, patient programmer 24 may permit patient 16 to adjust therapy parameters such as duration, amplitude, pulse width and pulse rate, within an adjustment range specified by the clinician via clinician programmer 22, or select from a plurality of stored stimulation therapy programs.

Stimulator 12, clinician programmer 22, and patient programmer 24 may communicate via cables or a wireless communication, as shown in FIG. 1A. Clinician programmer 22 and patient programmer 24 may, for example, communicate via wireless communication with neurostimulator 12 using RF telemetry techniques known in the art. Clinician programmer 22 and patient programmer 24 may also communicate with each other using any of a variety of local wireless communication techniques, such as RF communication according to the 802.11 or Bluetooth specification sets, infrared communication, e.g., according to the IrDA standard, or other standard or proprietary telemetry protocols.

Although described herein with reference to embodiments in which stimulator 12 adjusts therapy based on relative motion between accelerometers 17, 19, the invention is not so limited. For example, in other embodiments, one or both of programmers 22, 24 may employ any of the techniques described herein to adjust therapy based on relative motion between accelerometers 17, 19. The programmers may receive values from accelerometers 17, 19 directly via wireless communication with the accelerometers, or via wireless communication with stimulator 12. The programmers may implement therapy changes through wireless communication with stimulator 12.

Figure 2:
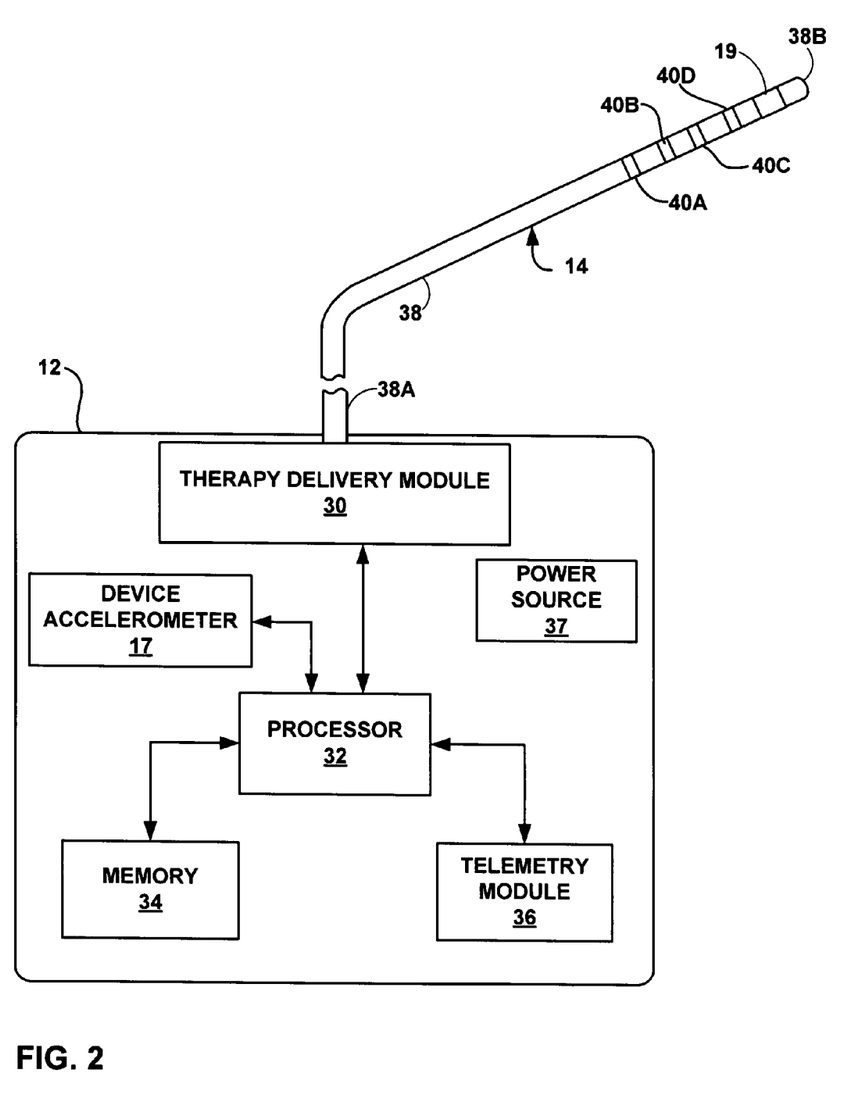
FIG. 2 is a block diagram illustrating various components of an electrical stimulator and an implantable lead.

FIG. 2 is a block diagram illustrating various components of stimulator 12 and an implantable lead 14. Stimulator 12 includes device accelerometer 17, therapy delivery module 30, processor 32, memory 34, telemetry module 36, and power source 37. Implantable lead 14 includes elongated lead body extending between proximal end 15A and distal end 15B. The lead body may be a cylindrical or may be a paddle-shaped (i.e., a "paddle" lead). Electrodes 40A, 40B, 40C, and 40D (collectively "electrodes 40") are disposed on the lead body adjacent to distal end 15B of lead 14.

In some embodiments, electrodes 40 may be ring electrodes. In other embodiments, electrodes 40 may be segmented or partial ring electrodes, each of which extends along an arc less than 360 degrees (e.g., 90-120 degrees) around the periphery of the lead body. In embodiments in which lead 14 is a paddle lead, electrodes 40 may be pad electrodes on one side of the lead body. Electrodes 40 extending around a portion of the circumference of lead body 38 or located on one side of a paddle lead may be useful for providing an electrical stimulation field in a particular direction and/or targeting a particular stimulation site. The configuration, type, and number of electrodes 40 illustrated in FIG. 2 are merely exemplary.

Lead 14 also includes lead accelerometer 19 coupled to the lead body. In the illustrated embodiment, lead accelerometer 19 is located proximate to distal end 15B of lead 14 and distal to electrodes 40. In other embodiments, lead accelerometer 19 may be positioned between individual electrodes 40 (e.g., between electrodes 40B and 40C) or proximal on lead 14 relative to electrodes 40. In preferred embodiments, lead accelerometer 19 is proximate to electrodes 40 in order to best detect the orientation and/or motion of the portion of lead 14 that includes electrodes 40. Lead accelerometer 19 may be coupled to an outer surface of, or located within, the lead body.

Stimulator 12 delivers stimulation therapy via electrodes 40 of lead 14. In particular, electrodes 40 are electrically coupled to a therapy delivery module 30 of stimulator 12 via conductors within lead 14. In one embodiment, a pulse generator or other signal generation circuitry within therapy delivery module 30 delivers electrical signals (e.g., pulses or substantially continuous-time signals, such as sinusoidal signals) to target stimulation site 18 (FIG. 1) via at least some of electrodes 40 under the control of a processor 32. The electrical signals may be delivered from therapy delivery module 30 to electrodes 40 via a switch matrix, which may be controlled by processor 32, and conductors carried by lead 14 and electrically coupled to electrodes 40.

Therapy delivery module 30, as well as the other components of stimulator 12 illustrated in FIG. 2, may be coupled to power source 37. Power source 37 may take the form of a small, rechargeable or non-rechargeable battery, or an inductive power interface that transcutaneously receives inductively coupled energy. In the case of a rechargeable battery, power source 37 similarly may include an inductive power interface for transcutaneous transfer of recharge power.

Processor 32 may include any number of processors (e.g., a main processor and one or more slave or sub-processors) and may include any one or more of a microprocessor, a controller, a digital signal processor (DSP), an application specific integrated circuit (ASIC), a field-programmable gate array (FPGA), discrete logic circuitry, or the like. Processor 32 controls the implantable signal generator within therapy delivery module 30 to deliver neurostimulation therapy according to selected stimulation parameters. For example, processor 32 may control therapy delivery module 30 to deliver electrical signals with selected amplitudes, pulse widths (if applicable), and rates. Processor 32 may also control therapy delivery module 30 to deliver the neurostimulation signals via selected subsets of electrodes 40 with selected polarities, i.e., selected electrode combinations or configurations.

At any given time, processor 32 may deliver stimulation according to a selected one or more of a plurality of programs stored in memory 34. Each program may include respective values for each of a plurality therapy parameters, such as respective values for each of amplitude, pulse width, pulse rate and electrode combination. Processor 32 may also control therapy delivery module 30 to deliver each signal according to a different program, thereby interleaving programs to simultaneously treat different symptoms or provide a combined therapeutic effect.

Memory 34 of neurostimulator 12 may include any volatile or non-volatile media, such as a random access memory (RAM), read-only memory (ROM), non-volatile RAM (NVRAM), electronically-erasable programmable ROM (EEPROM), flash memory, and the like. In some embodiments, memory 34 of neurostimulator 12 may store multiple programs that are available to be selected by patient 16 via patient programmer 24 (FIG. 1) or a clinician via clinician programmer 22 (FIG. 1) for delivery of neurostimulation therapy. For example, memory 34 may store programs transmitted by clinician programmer 22 (FIG. 1). Memory 34 also stores program instructions that, when executed by processor 32, cause stimulator 12 to deliver neurostimulation therapy, and provide the other functionality described herein. Accordingly, computer-readable media storing instructions may be provided to cause processor 32 to provide functionality as described herein.

Processor 32 controls telemetry module 36 to exchange information with an external programmer, such as clinician programmer 22 and/or patient programmer 24 (FIG. 1), by wireless telemetry. In addition, in some embodiments, telemetry module 36 supports wireless communication with one or more wireless sensors that sense physiological signals and transmit the signals to stimulator 12.

Processor 32 also interfaces with device and lead accelerometers 17 and 19. Device accelerometer 17 may be coupled to the housing of stimulator 12 or located within stimulator 12. In either case, device accelerometer 17 senses the movement and orientation of stimulator 12, while lead accelerometer 19 senses the movement or orientation of the distal portion of lead 14 proximate to electrodes 40.

The signals sensed via device accelerometer 17 as well as those sensed via lead accelerometer 19 may be sent to processor 32 for analysis. Processor 32 may include any number of processors. In some embodiments, processor 32 may comprise a first processor that controls therapy delivery module 30 to deliver therapy to patient 16 (e.g., a main processor) and a second processor dedicated to receiving and analyzing the signals obtained from device accelerometer 17 and lead accelerometer 19 (e.g., a slave or sub-processor). The second processor may provide the first processor with results from the analysis of the accelerometer signals. Processor 32 may compare the signals from the accelerometers, e.g., calculate the difference between the signals received from device accelerometer 17 and lead accelerometer 19 or some other value, to determine the relative movement or orientation of stimulator 12 and lead 14. For multi-axis accelerometers, calculating the difference may involve calculating the difference between each of the axial signals (X, Y, and Z) generated by each of the accelerometers. This calculation may be performed substantially in real-time.

Processor 32 may also control therapy delivery module 30 to deliver therapy to patient 16 based on the relative orientation or movement of stimulator 12 and lead 14. As will be described in further detail below, the electrodes selected to deliver the stimulation signal and their polarities may be adjusted based on the relative orientation and/or motion of device accelerometer 17 and lead accelerometer 19. In some embodiments, a stimulation amplitude, pulse width, pulse rate, or other therapy parameters may be also adjusted based on the relative orientation and/or motion of device accelerometer 17 and lead accelerometer 19. Adjustments to the therapy delivered to patient 16 may be made substantially in real-time as patient 16 transitions between postures.

Figure 3A:
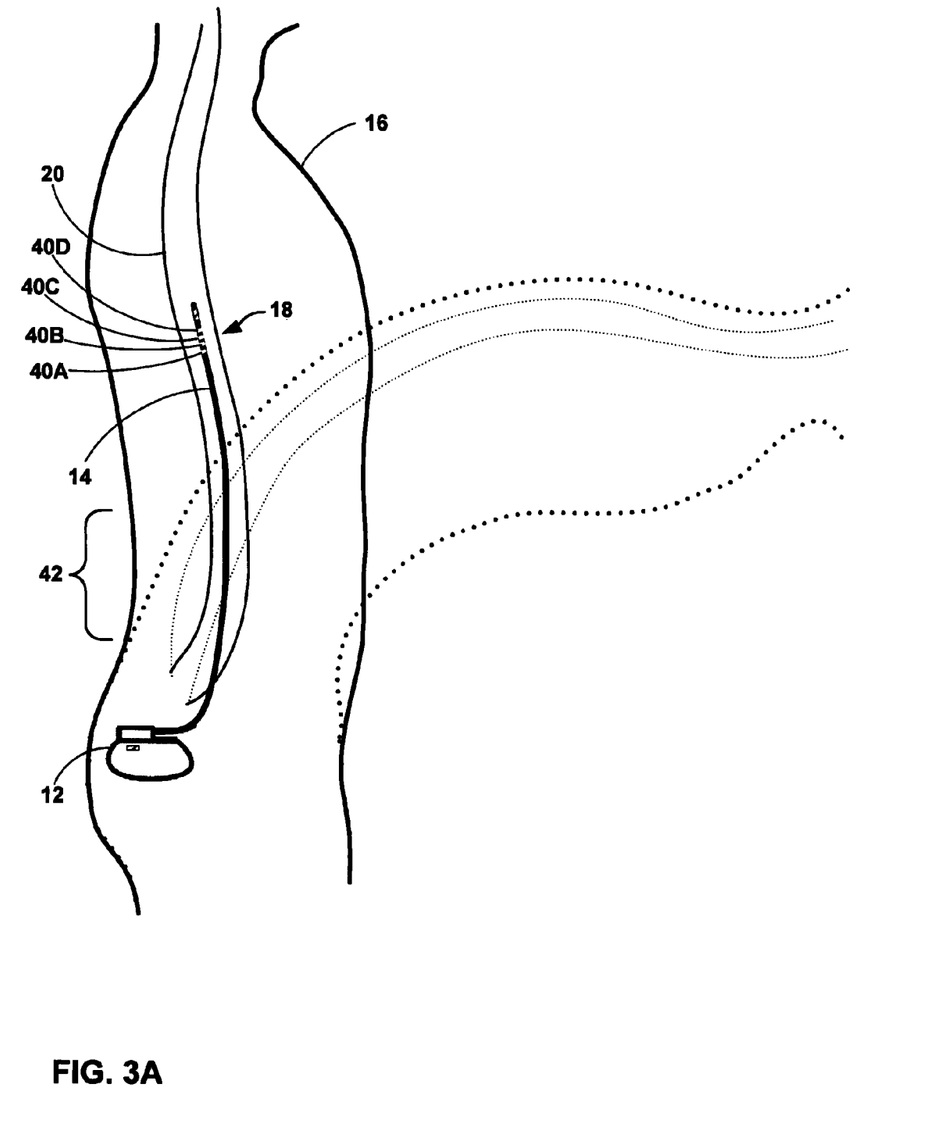
FIGS. 3A and 3B illustrate how the position of electrodes on a lead 14 relative to a target stimulation site may change as patient 16 changes posture.
Figure 3B:
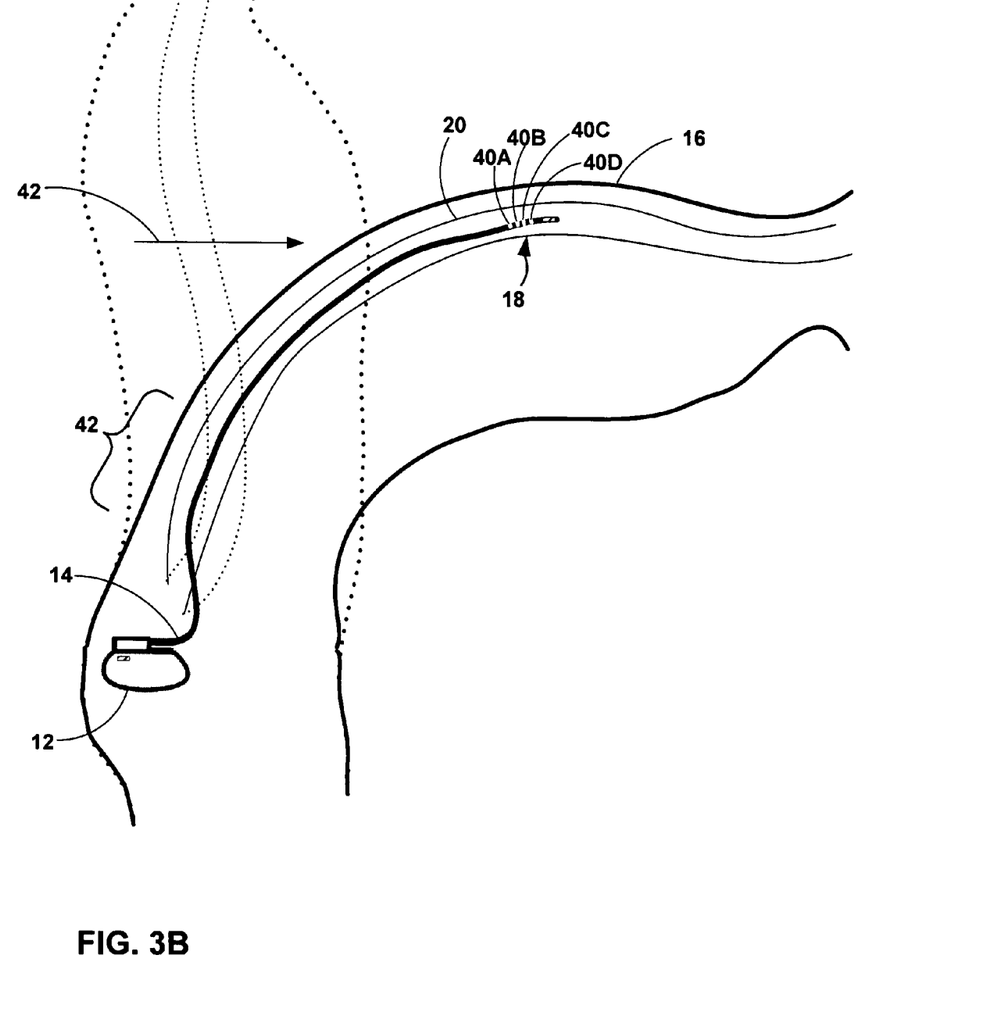

FIGS. 3A and 3B illustrate how the position of lead 14 may change as patient 16 changes posture. FIG. 3A illustrates patient 16 in an upright position, and FIG. 3B illustrates patient 16 bending forward at the waist. For purposes of comparison, patient 16 is shown bent forward in phantom lines in FIG. 3A, and the upright position of patient 16 is shown in phantom lines in FIG. 3B.

Lead 14 extends from stimulator 12 implanted in the buttock of patient 16 along spinal cord 20 (e.g., though the epidural space) to target stimulation site 18 in the middle or upper back of patient 16. When patient 16 is in an upright position, as illustrated in FIG. 3A, lead 14 follows the concavity of lower back 42 of patient 16. In FIG. 3B, when patient 16 is bent forward, lower back 42 is extended to a substantially straight or slightly convex position, and lead 14 conforms to the extended position of lower back 42.

Since lead 14 is attached to stimulator 12, it is unable to move with stimulation site 18 as patient 16 changes posture. Accordingly, the position of electrodes 40 relative to target stimulation site 18 may vary based on the posture of patient 16. For example, in the upright position illustrated in FIG. 3A, target stimulation site 18 may be approximately centered between electrodes 40A and 40B. When patient 16 is bent forward, as illustrated in FIG. 3B, electrodes 40 on lead 14 may move such that target stimulation site 18 is located between electrodes 40C and 40D. In FIG. 3B, the position of the distal end of lead 14 relative to spinal cord 20 prior to patient 16 bending over is illustrated by phantom lines 44.

The electrodes selected to deliver stimulation therapy and/or their polarities may be modified based on the posture of patient 16. For example, a first set of electrodes may be selected to deliver therapy when patient 16 is in a first position, and a second set of electrodes may be selected to deliver therapy when patient 16 is in a second position. The first and second positions may be indicated by the relative movement and orientations of accelerometers 17, 19 (FIGS. 1 and 2).

Tracking the relative movement and orientation of device accelerometer 17 and lead accelerometer 19 may allow therapy parameters to be adjusted to maintain focus on target stimulation site 18. For example, the relative movement and orientation of device accelerometer 17 and lead accelerometer 19 may be used to detect the transition of patient 16 from the upright position illustrated in FIG. 3A to the forward bent position illustrated in FIG. 3B and appropriately modify which electrodes are used to deliver stimulation. Continuous posture sensing via device accelerometer 17 and lead accelerometer 19 may allow the therapy to be adjusted as necessary to maintain continuous focus on target stimulation site 18. Device accelerometer 17 and lead accelerometer 19 may provide direct sensor feedback that allows the therapy delivered to patient 16 to be adjusted as patient 16 is moving and allows therapy efficacy to be maintained throughout the patient's range of motion.

Relationships between posture, as indicated by a relative movement and orientation of accelerometers 17 and 19, and effective therapy parameters, such as which electrodes are selected to deliver therapy, may be programmed or learned. For example, a clinician or patient may program stimulator 12 to adjust one or more therapy parameters based on the posture of patient 16.

During a programming session, patient 16 may take on a variety of postures, and the therapy parameters may be optimized in each posture. The relative orientation of accelerometers 17, 19 may also be determined in each posture. Stimulator 12 may store the programmed therapy parameters, e.g., therapy programs, specific to each posture in association with an indication of the relative orientation. After such a programming session, stimulator 12 may adjust the therapy delivered to patient 16 based on the posture of patient 16 by, for example, periodically identifying the relative orientation of accelerometers 17, 19 based on the signals generated by the accelerometers, and selecting a program associated with the relative orientation.

In some embodiments, the relationships between posture and effective therapy parameters may be learned. More specifically, stimulator 12 may "learn" to provide closed-loop therapy based on therapy adjustments made by patient 16. For example, a patient may adjust one or more therapy parameters, or select a new predetermined program, as necessary. Stimulator 12 may correlate the patient's posture, e.g., relative movement and orientation of accelerometers 17, 19 as indicated by a comparison of their signals, when the therapy was adjusted with the adjusted therapy parameters or program. Processor 32 of stimulator 12 may store relative signal values, e.g., differences between signals, and programs in a look-up table or other data structure.

In some embodiments, stimulator 12 may automatically apply the adjusted therapy parameters whenever patient 16 returns to that posture. In some embodiments, stimulator 12 may ask patient 16 whether or not to store the adjusted therapy parameters. This may allow automatic adjustment of therapy parameters in a manner desired by patient 16 as the sensed posture of patient 16 changes. Stimulator may learn associations of relative accelerometer movements and/or orientations with programs, and subsequently deliver therapy according to programs associated with relative accelerometer movements and/orientations, using any of the techniques described in commonly-assigned and copending U.S. patent application Ser. No. 11/414,625, entitled, "CLOSED-LOOP THERAPY ADJUSTMENT" and filed on Apr. 28, 2006, U.S. patent application Ser. No. 11/607,454, entitled, "CLOSED-LOOP THERAPY ADJUSTMENT" and filed on Dec. 1, 2006, and U.S. patent application Ser. No. 11/607,426, entitled, "CLOSED-LOOP THERAPY ADJUSTMENT" and filed on Dec. 1, 2006, the entire content of each of which is incorporated herein by reference.

In other embodiments, a basic body model may be used to aid in adjusting therapy parameters based on the posture of patient 16. For example, the basic body model may calculate the relative motion or position of lead 14 with respect to target stimulation site 18 based on the relative motion or position of device accelerometer 17 and lead accelerometer 19. The basic body model may include a variety of algorithms based on kinesiology and the biomechanics of the human body. In some embodiments, the basic body model may be implemented using algorithms or a series of lookup tables. In some embodiments, the basic body model may require user inputs regarding characteristics of patient 16 and therapy system 10 (FIG. 1). For example, the implant locations of neurostimulator 12 and lead 14, the length of lead 14, and the length of lead 14 from distal end 15B and/or electrodes 40 to a lead anchor, and/or the height and gender of patient 16 may be inputted into the basic body model. The basic body model may analyze the relative motion and orientation of device accelerometer 17 and lead accelerometer 19 and determine how the position of electrodes 40 of lead 14 may have changed relative to target stimulation site 18.

In some embodiments, therapy parameters may be automatically adjusted based on the analysis provided by the basic body model. In other embodiments, the analysis provided by the basic body model may compliment a programming session or learning mode. For example, during a programming session the basic body model may provide a starting point or suggestion of how to adjust therapy parameters based on posture. The clinician or patient may implement the therapy suggested by the basic body model and/or fine tune the therapy to better treat the symptoms of patient 16. Likewise, during a learning mode the therapy suggested by the basic body model may be implemented (e.g., automatically or manually) and/or fine tuned by patient 16.

Figure 4A:
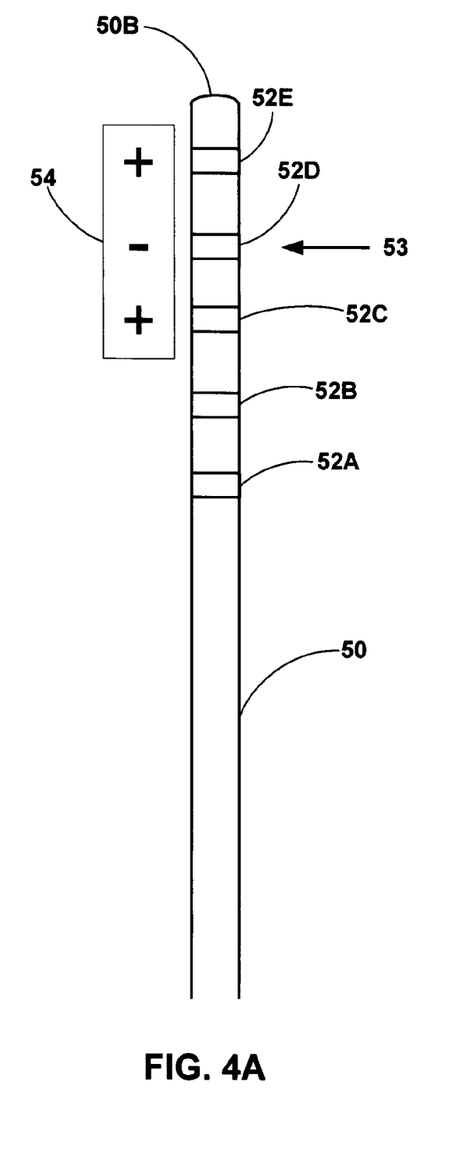
FIGS. 4A and 4B illustrate an example of how therapy parameters may be adjusted based on the motion of the electrodes carried by a lead relative to a target stimulation site.
Figure 4B:
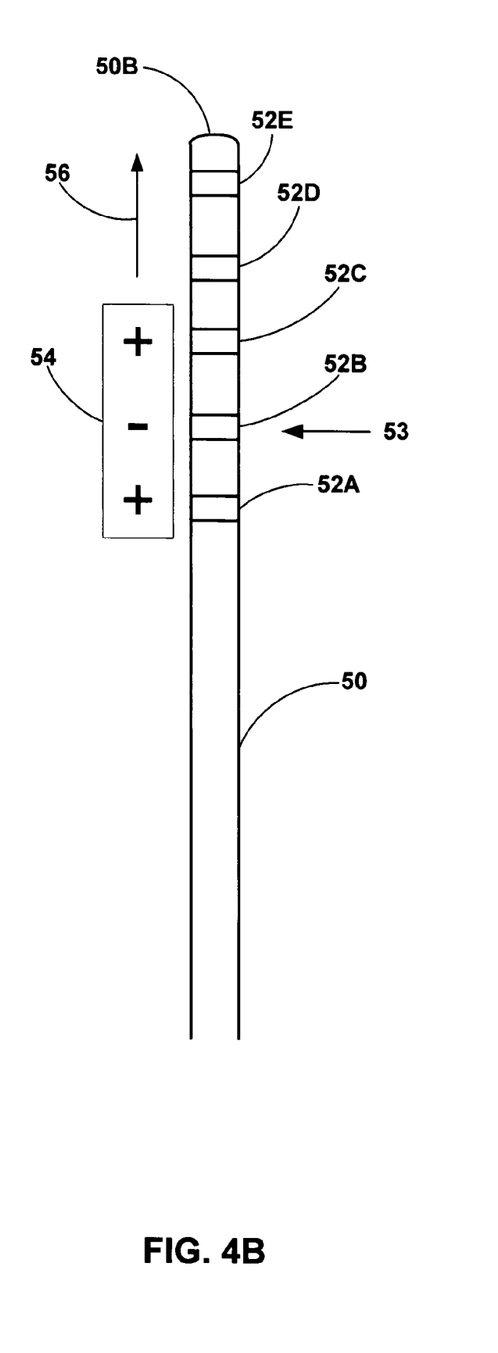

FIGS. 4A and 4B illustrate an example of how therapy parameters may be adjusted based on the motion of the electrodes carried by a lead relative to a target stimulation site. Lead 50 includes electrodes 52A-52H (collectively "electrodes 52") proximal to distal end 51 of lead 50. Electrodes 52 may be programmed to deliver therapy to target stimulation site 53. For example, as illustrated in FIG. 4A, electrodes 52 may be programmed to deliver therapy to target stimulation site 53 via an electrode configuration including electrodes 52F-52H with the illustrated polarities 54. More specifically, electrodes 52F and 52H may be activated as anodes and electrode 52G may be activated as a cathode to deliver therapy to target stimulation site 53.

FIG. 4B illustrates an embodiment in which lead 50 has moved in direction 56 relative to the position of lead 50 illustrated in FIG. 4A and target stimulation site 53. In order to effectively deliver therapy to target stimulation site 53, electrodes 50D and 50F may be activated as anodes and electrode 50E may be activated as a cathode according to a new electrode configuration. This may allow the therapy delivered to target stimulation site 53 in FIG. 4B to remain substantially the same as the therapy delivered to target stimulation site 53 in FIG. 4A despite the movement of electrodes 52 relative to target stimulation site 53. In some embodiments, the electrode configuration may change to include different numbers of electrodes or different arrangements of cathodes and anodes as patient 16 moves, rather than merely shifting a grouping of anodes and cathodes along a lead, to create virtual electrodes proximate to target stimulation site 53.

Figure 5A:
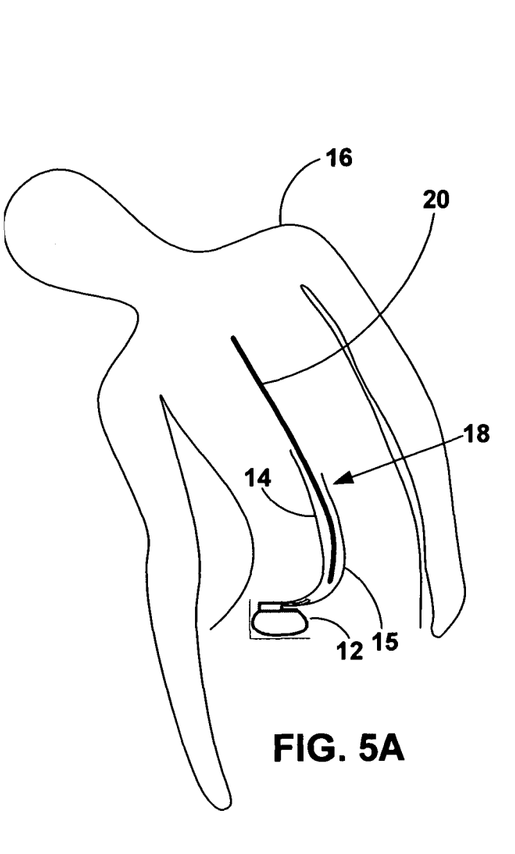
FIGS. 5A-5C illustrate two leads coupled to a stimulator to deliver bilateral stimulation.
Figure 5B:
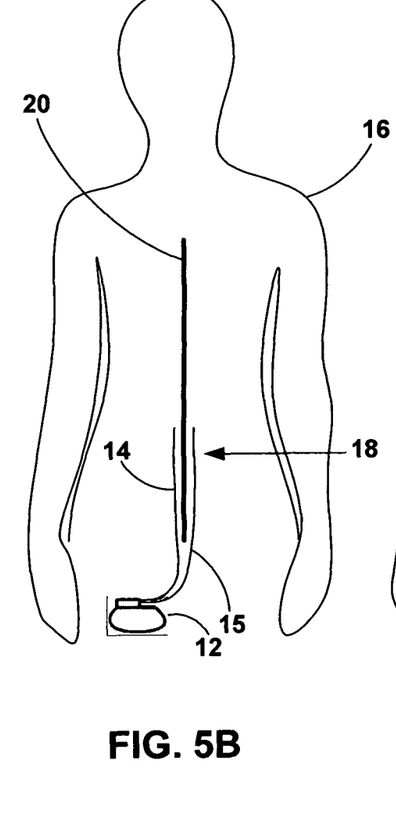
Figure 5C:
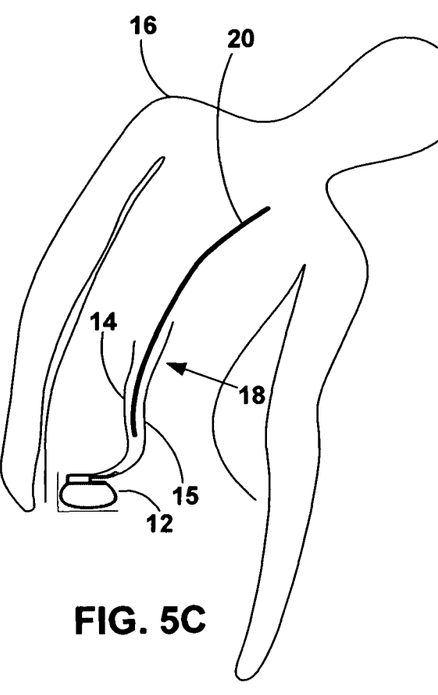

In some embodiments, multiple leads are coupled to stimulator 12 to deliver therapy to target stimulation site 18 of patient 16. For example, FIGS. 5A-5C illustrate leads 14 and 15 coupled to stimulator 12 to deliver bilateral stimulation. In some embodiments, each of leads 14 and 15 may include a respective lead accelerometer (not shown). FIG. 5B illustrates patient 16 in an upright position with lead 14 implanted on one side of spinal cord 20 and lead 15 implanted on the opposite side of spinal cord 20. FIGS. 5A and 5C illustrate how leads 14 and 15 may move relative to target stimulation site 18 when patient 16 bends to the side.

As shown in FIGS. 5A and 5C, leads 14 and 15 may move in opposite directions as patient 16 bends to the side. When patient 16 transitions to other postures, such as the forward bent position illustrated in FIG. 3B, leads 14 and 15 may both move in the same direction. Providing lead accelerometer on each of leads 14 and 15 may provide useful information regarding how each of leads 14 and 15 move relative to target stimulation site 18. In other embodiments, only one of leads 14 and 15 may include a lead accelerometer, and the position of the other lead relative to target stimulation site 18 may be determined using the basic body model and/or the implant locations of the leads. Therapy adjustments may address different movement directions by different leads by, for example, moving active anodes and cathodes on each of the leads in different axial directs to keep them proximate to one or more target stimulation sites.

Figure 6:
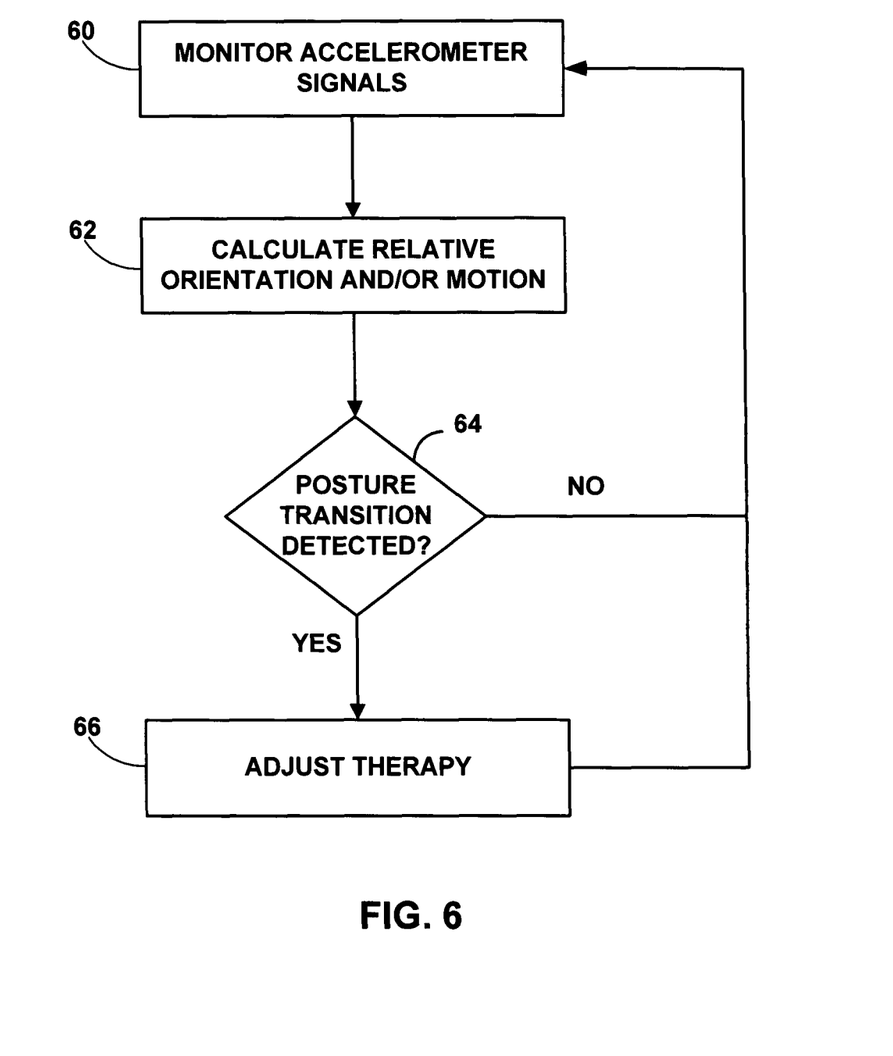
FIG. 6 is a flow chart illustrating an example technique for controlling therapy based on relative orientation of and/or motion between stimulator and lead-borne sensors.

FIG. 6 is a flow chart illustrating an example technique for controlling therapy based on relative motion between stimulator and lead-borne sensors. Signals from device accelerometer 17 and lead accelerometer 19 may be monitored, for example, via processor 32 (60). Based on the signals received from device accelerometer 17 and lead accelerometer 19, the relative orientation and/or motion of device accelerometer 17 and lead accelerometer 19 may be calculated (62). This calculation may be performed substantially in real-time and may be indicative of the posture of patient 16. If a posture change is detected based on the relative orientations of device accelerometer 17 and lead accelerometer 19, processor 32 may adjust the therapy delivered to patient 16 based on the relative orientation and/or motion to compensate for movement of electrodes relative to a target site due to the posture change (64).

The relative orientations of the accelerometers as indicated by their respective orientations with respect to ground, i.e., the Earth's gravity, may be used to detect posture of the patient and posture transitions. Furthermore, the characteristics of the raw accelerometer signals generated by device accelerometer 17 and lead accelerometer 19 that indicate relative motion or movement between the accelerometers may be used in combination with or instead of the relative orientations of device accelerometer 17 and lead accelerometer 19 to identify posture changes and adjust the therapy delivered to patient 16. For example, the amplitudes and rate of change of the amplitudes of the raw accelerometer signals may be used to determine the direction patient 16 is moving (e.g., bending) and how quickly patient 16 is changing posture. Processor 32 may adjust the therapy delivered to patient 16 based on the relative orientation of accelerometers 17 and 19, the direction patient 16 is moving, and/or the rate at which patient 16 is moving.

In some embodiments, the therapy is adjusted according to therapy parameters programmed into stimulator 12 or learned by stimulator 12. Additionally or alternatively, adjustments to the therapy delivered to patient 16 may be based on a basic body model. As discussed above, some embodiments may include a data structure that associates a plurality of values of relative orientation, e.g., differences between the signals generated by accelerometers 17, 19, with respective stimulation programs.

Transitions between two programs based on changes in the relative orientation of accelerometers 17, 19 may be implemented via any suitable technique. In one embodiment, processor 32 provides instructions that cause therapy module 30 to time-interleave stimulation energy between the electrode combinations of the programs as described in commonly-assigned U.S. patent application Ser. No. 11/401,100, entitled, "SHIFTING BETWEEN ELECTRODE COMBINATIONS IN ELECTRICAL STIMULATION DEVICE," and filed on Apr. 10, 2006, the entire content of which is incorporated herein by reference. In the time-interleave shifting embodiment, the amplitudes of the first and second electrode combinations are ramped downward and upward, respectively, in incremental steps until the amplitude of the second electrode combination reaches a target amplitude and the amplitude of the first combination reaches zero.

In another embodiment, shifting electrical stimulation and in particular, the current, between two electrode combinations of respective therapy programs is achieved by reducing an amplitude delivered to an electrode of one combination relative to the increase in amplitude an electrode of another combination. In such embodiments, therapy module 30 (FIG. 2) may include at least two current sources. It may be desirable to maintain the current at a relatively consistent perceptual intensity for patient 16 in order to prevent the current from exceeding a maximum threshold for patient 16, above which, patient 16 may feel pain or discomfort.

Furthermore, in some embodiments, when processor 32 identifies a relative orientation that is not associated with a therapy program, e.g., in a data structure, processor 32 may generate an intermediary program between entries in the data structure by interpolation, e.g. linear, non-liner, or other. Processor 32 may employ any of the techniques described in commonly-assigned U.S. patent application Ser. No. 11/799,035, entitled "THERAPY ADJUSTMENT," filed on Apr. 30, 2007 and/or U.S. patent application Ser. No. 11/799,112, entitled "THERAPY ADJUSTMENT," filed on Apr. 30, 2007. The entire content of each of these Applications is incorporated herein by reference.

Various embodiments of the invention have been described. These and other embodiments are within the scope of the following claims.

The invention claimed is:

1. A system comprising: an electrical stimulator comprising a device accelerometer; a lead coupled to the electrical stimulator configured to deliver stimulation from the electrical stimulator to a target stimulation site in a patient, the lead comprising a lead accelerometer; a processor configured to receive a first signal from the device accelerometer and a second signal from the lead accelerometer, compare the first signal to at least the second signal to detect at least one of a posture or posture transition of the patient, and control delivery of the stimulation to the patient based on the detection, wherein the processor is configured to detect the at least one of the posture or posture transition of the patient based on a relative orientation of the device accelerometer and the lead accelerometer based on the comparison of the first and second signals.

2. The system of claim 1, wherein the processor is configured to detect the at least one of the posture or posture transition of the patient based on a relative motion of the device accelerometer and the lead accelerometer based on the comparison of the first and second signals.

3. The system of claim 1, wherein the lead accelerometer is proximate to a distal end of the lead body.

4. The system of claim 1, wherein the electrical stimulator comprises a housing, and the device accelerometer is located within the housing.

5. The system of claim 1, wherein the lead accelerometer is located within the lead.

6. The system of claim 1, wherein the lead comprises a plurality of electrodes, and the processor is configured to control which of the plurality of electrodes are selected to deliver the therapy based on the detection of the at least one of the posture or posture transition of the patient.

7. The system of claim 6, wherein the lead accelerometer is located proximate to the electrodes.

8. The system of claim 1, wherein each of the device accelerometer and the lead accelerometer comprises a multi-axis accelerometer.

9. The system of claim 8, wherein the processor is configured to calculate a difference between the first signal from the device accelerometer and the second signal from the lead accelerometer for each of a plurality of axes to detect the at least one of the posture or posture transition of the patient.

10. The system of claim 1, wherein the stimulation comprises spinal cord stimulation.

11. The system of claim 1, wherein the electrical stimulator is implantable.

12. The system of claim 1, wherein the processor comprises a processor of the electrical stimulator.

13. The system of claim 1, wherein the processor is configured to calculate a difference between the first signal from the device accelerometer and the second signal from the lead accelerometer to detect the at least one of the posture or posture transition of the patient.

14. A method comprising:
receiving a first signal from a device accelerometer and a second signal from a lead accelerometer, wherein the device accelerometer is located on or within an electrical stimulator that delivers stimulation to a patient, and wherein the lead accelerometer is coupled to a lead that delivers the stimulation from the electrical stimulator to the target stimulation site of the patient;
comparing the first signal to at least the second signal to detect at least one of a posture or posture transition of the patient;
detecting the at least one of the posture or posture transition of the patient based on a relative orientation of the device accelerometer and the lead accelerometer based on the comparison of the first and second signals; and
controlling delivery of the stimulation by the electrical stimulator based on the detection.

15. The method of claim 14, wherein detecting the at least one of the posture or posture transition of the patient comprises detecting the at least one of the posture or posture transition of the patient based on a relative motion of the device accelerometer and the lead accelerometer based on the comparison of the first and second signals.

16. The method of claim 14, wherein the lead comprises a plurality of electrodes, and wherein controlling delivery of the stimulation to the patient based on the detection comprises controlling which of the plurality of electrodes are selected to deliver the therapy based on the detection.

17. The method of claim 16, wherein the lead accelerometer is located proximate to the electrodes.

18. The method of claim 14, wherein each of the device accelerometer and the lead accelerometer comprises a multi-axis accelerometer.

19. The method of claim 18, wherein comparing the first signal to at least the second signal comprises calculating a difference between the first signal from the device accelerometer and the second signal from the lead accelerometer for each of a plurality of axes to detect the at least one of the posture or posture transition of the patient.

20. The method of claim 14, wherein the stimulation comprises spinal cord stimulation.

21. The method of claim 14, wherein controlling delivery of the stimulation comprises controlling delivery of the stimulation substantially in real-time based on the signals received from the device accelerometer and the lead accelerometer.

22. The method of claim 14, further comprising determining a value based on the comparison of the first signal to at least the second signal to detect the at least one of the posture or posture transition of the patient, wherein controlling delivery of the therapy by the electrical stimulator comprises controlling delivery of the therapy according to a stimulation program previously associated with the value in a data structure.

23. The method of claim 22, wherein the stimulation program is associated with the value during a programming session.

24. The method of claim 22, wherein the stimulation program is associated with the value using a learning mode.

25. The method of claim 22, wherein the stimulation program is associated with the value using an algorithmic model of a human body.

26. A medical device comprising:
a therapy module configured to deliver stimulation to a patient via a lead;
a device accelerometer; and
a processor configured to receive a first signal from the device accelerometer and a second signal from a lead accelerometer on the lead, compare the first signal to at least the second signal to detect at least one of a posture or posture transition of the patient, and control delivery of the stimulation by the therapy module based on the detection, wherein the processor is configured to detect the at least one of the posture or posture transition of the patient based on a relative orientation of the device accelerometer and the lead accelerometer based on the comparison of the first and second signals.

27. The medical device of claim 26, wherein the processor is configured to calculate a difference between the first signal from the device accelerometer and the second signal from the lead accelerometer to detect the at least one of the posture or posture transition of the patient.

* * * * *